(12) United States Patent
Wang (10) Patent No.: US 9,554,734 B2
(45) Date of Patent: Jan. 31, 2017

(54) DISPOSABLE AUTOMATIC PAINLESS SAFE HEMOSTIX

(76) Inventor: Lin Wang, Zhejiang (CN)

( * ) Notice: Subject to any disclaimer, the term of this patent is extended or adjusted under 35 U.S.C. 154(b) by 375 days.

(21) Appl. No.: 13/642,128

(22) PCT Filed: Apr. 21, 2011

(86) PCT No.: PCT/CN2011/073131
§ 371 (c)(1),
(2), (4) Date: Oct. 19, 2012

(87) PCT Pub. No.: WO2011/131138
PCT Pub. Date: Oct. 27, 2011

(65) Prior Publication Data
US 2013/0035708 A1    Feb. 7, 2013

(30) Foreign Application Priority Data

Apr. 22, 2010    (CN) .......................... 2010 1 0152580

(51) Int. Cl.
*A61B 5/15*    (2006.01)
*A61B 5/151*    (2006.01)

(52) U.S. Cl.
CPC .......... *A61B 5/1411* (2013.01); *A61B 5/1513* (2013.01); *A61B 5/150022* (2013.01); *A61B 5/15109* (2013.01); *A61B 5/15111* (2013.01); *A61B 5/15117* (2013.01); *A61B 5/15142* (2013.01); *A61B 5/15144* (2013.01); *A61B 5/150198* (2013.01); *A61B 5/150412* (2013.01); *A61B 5/150519* (2013.01); *A61B 5/150549* (2013.01); *A61B 5/150618* (2013.01); *A61B 5/150916* (2013.01)

(58) Field of Classification Search
CPC ............ A61B 5/150022; A61B 5/0412; A61B 5/15186; A61B 5/1411
USPC ... 606/181–183, 172; 600/583; 604/136–139
See application file for complete search history.

(56) References Cited

U.S. PATENT DOCUMENTS

| | | | | |
|---|---|---|---|---|
| 5,582,184 | A * | 12/1996 | Erickson et al. ............. | 600/576 |
| 2006/0116705 | A1* | 6/2006 | Schraga ........................ | 606/181 |
| 2007/0083222 | A1* | 4/2007 | Schraga ........................ | 606/181 |
| 2008/0077167 | A1* | 3/2008 | Flynn et al. .................. | 606/172 |
| 2009/0069833 | A1* | 3/2009 | Li .................................. | 606/182 |
| 2011/0029006 | A1* | 2/2011 | Leong ........................... | 606/182 |

FOREIGN PATENT DOCUMENTS

| | | | | |
|---|---|---|---|---|
| EP | 0633004 A1 * | 1/1995 | ............. | A61B 19/02 |
| EP | 0747006 A1 * | 12/1996 | ............... | A61B 5/14 |

* cited by examiner

*Primary Examiner* — Kathleen Holwerda
*Assistant Examiner* — Socrates L Boutsikaris
(74) *Attorney, Agent, or Firm* — Global IP Services; Tianhua Gu (57) ABSTRACT

A disposable automatic painless safe hemostix includes an outer casing, an inner sleeve, a needle module and a spring. The needle module is snapped in the inner sleeve and the outer casing. The needle module has a needle point protecting pole. Interlock fixing faces and protrusions are provided on the inner sleeve. Interlock guiding slopes and protrusion stoppers are provided on the inner wall of the outer casing. One end of the interlock engages the interlock fixing face, and the other end engages the interlock guiding slope.

6 Claims, 13 Drawing Sheets

DISPOSABLE AUTOMATIC PAINLESS SAFE HEMOSTIX

CROSS REFERENCE TO RELATED PATENT APPLICATION

The present application is the US national stage of PCT/CN2011/073131 filed on Apr. 21, 2011, which claims the priority of the Chinese patent application No. 201010152580.8 filed on Apr. 22, 2010 which application is incorporated herein by reference.

FIELD OF THE INVENTION

The present invention relates to a hemostix, particularly a disposable automatic painless safe hemostix.

DESCRIPTION OF THE PRIOR ART

A hemostix is a tool to pierce human skin and get the sample blood. Common hemostixes are divided into the following four kinds:

1. Common Hemostix

A common hemostix wraps a stainless steel needle in a plastic structure by injection molding. The place wrapping the needle point is provided with a groove that is easily broken by twisting and allowing the needle point to expose. The flat exterior wrapping the needle point is convenient for applying a twisting force to the plastic layer wrapping the needle point. During operation, twist exterior flat place to break the exterior plastic wrapping needle point and allow the needle point to expose, and then pierce the skin of the place for blood sampling to complete blood sampling operation. After using once, the hemostix should be disposed. Some hemostixes replace the flat place to apply twisting force with a Belleville cap. When the hemostix is to be disposed, cover the needle point with the Belleville cap to protect the operator from the needle point. However, there is still the possibility of second use of the needle tube and being unintentionally injured.

2. Pen Hemostix

A pen hemostix is like a sign pen that is provided with an intermediate section of thread connection including a chute. A needle fixing seat is provided in the chute and a spring is provided at the rear end of the needle fixing seat. A handle connecting the needle fixing seat and an initiating button like a trigger are provided outside the intermediate section; during operation, unscrew the pen hemostix and remove the jacket in front end, take a hemostix like above-mentioned kind (since the difference between the mounting seats inside different hemostixes requires corresponding special hemostixes), twist and break the plastics wrapping needle point to allow needle point to expose, put the needle into a needle mounting seat, restore the separated thread of jacket to the body of hemostix; pull exterior connecting handle to allow the springs in the rear end of needle mounting seat to be compressed simultaneously until the needle mounting seat and the trigger snap in position to complete blood sampling preparation; press the central hole of the front end of hemostix against the blood sampling position, press initiating button and the inner trigger will release needle mounting seat, spring tension will allow needle mounting seat to carry needle point towards the blood sampling position to puncture skin layer, thus completing the action of blood sampling; finally unscrew and separate the jacket once again, remove and dispose the needle used, and restore the separated jacket to its body, thus completing the entire operation. A part of the above-mentioned hemostixes is provided with Belleville caps at twisting place. Cover the needle point with the caps before disposal to avoid injuring anybody else unintentionally later. The whole procedure is therefore loaded down with trivial details and requires much time, and there exists the possibility of second use of the needle tube and being unintentionally injured.

3. A Disposable Safe Hemostix

This disposable safe hemostix comprises a casing, a needle module wrapping s stainless steel needle tube, a spring (or elastic means) and an initiating button. The spring is nested in the frontal end of needle module and installed in the cavity of casing in such a manner that the needle module exposes out of the transpiercing central hole in the front end of the casing to allow the initiating button to be mounted. During operation, first unscrew the frontal end and expose the forcing handle of needle module, break the plastic layer wrapping the needle and remove the needle to the extent that the needle point of needle module exposes to the interior of casing, or remove the hood, press the frontal hole against the blood sampling position and press a twisting force to the initiating button by a finger, or directly apply a force by holding the casing to the extent that the spring is compressed to allow needle point to expose out of the central hole and puncture the skin of blood sampling position, thus completing the operation of blood sampling. After releasing the hemostix, the spring tension will force the needle point to withdraw to the casing, thus preventing the needle point from injuring anybody else.

4. Another Disposable Safe Hemostix

This disposable safe hemostix comprises a casing, a needle module wrapping s stainless steel needle tube and a spring. The casing takes a form of hollow square structure for mounting needle module, wherein one end of the outside is provided with a pressing handle like a trigger. The trigger extends into a hollow hole to lock and unlock the needle module; the needle module is provided in the cavity of casing; a reinforcement wing plate provided at needle point side of needle module for applying twisting force exposes out of the casing, and a fixing spring is mounted in an inverted direction. During operation, first push the reinforcement wing plate into the casing to compress the spring until it is fixed with the trigger; twist the reinforcement wing plate to break the plastic layer wrapping the needle, remove the broken reinforcement wing plate to allow the needle point to expose (hiding inside the central hole of inner sleeve), press the blood sampling position against the blood sampling hole, press the handle of trigger mounted on the casing to release the needle module. The spring tension will force the needle point of needle module to puncture skin layer of blood sampling position, and later spring tension will force the needle point to withdraw in the central hole of inner sleeve to avoid the needle point from injuring anybody else.

All the above-mentioned four kinds of product have some shortcoming in structure: Though many blood sampling products such as hemostix added the structure of Belleville cap for protecting the needle point before disposal, yet the needle point exposes in the course of operation and it is hard to avoid unintentional injuring, particularly in the case of a second man or medical care personnel assisting blood sampling and disposing with the Belleville cap.

As for the third kind of safe hemostix, the pressing force to puncture skin layer easily makes patients feeling nervous and painful.

Though the fourth kind of safe hemostix has a certain improvement over the third kind, yet the action of pushing reinforcement wing plate into a casing until the compressed spring is fitted with a trigger most probably unintentionally contacts the handle of trigger in the casing, thus damaging and wasting the hemostix. Moreover, in the event an operator does not first push the reinforcement wing plate to enable the compressed spring to be fitted with the trigger in correct order but directly rotate the reinforcement wing plate to break the plastic layer wrapping the needle, the hemostix will also be damaged and wasted.

SUMMARY OF THE INVENTION

Accordingly, the present invention has been keeping in mind the above problems occurring in the related art, such as complicated procedure, waste easily caused by maloperation, and difficulty to prevent using twice and unintentional injury, and provided a disposable automatic painless safe hemostix that is characterized by convenient operation and complete prevention of using twice and unintentional injury.

In an effort to overcome the above problems, the present invention provides a technical solution as follows:

A disposable automatic painless safe hemostix comprises a jacket, an inner sleeve, a needle module and a spring. A puncturing needle tube is provided inside the needle module. One end of the needle module is nested in the inner sleeve and other end extends in the jacket. The inner sleeve is provided with a falcula fixing surface and a male fitting. The needle module is provided with a falcula. The inner wall of jacket is provided with a falcula-oriented slant and a male fitting limit reinforcement. One end of the falcula fits the falcula fixing surface and the other end fits the falcula-oriented slant.

Preferably, the inner wall of jacket is provided with an inner sleeve closed fixing convex reinforcement. The inner sleeve closed fixing convex reinforcement is provided with an emboss. The outer wall of inner sleeve is provided with a groove that fits the emboss.

The falcula comprises a falcula connecting reinforcement and a falcula button. The falcula connecting reinforcement is connected with the falcula and extends to the right end. The falcula button is provided at the right end of falcula connecting reinforcement and is also provided with a falcula interface to fit the falcula fixing surface.

Preferably, the said inner sleeve is provided with a needle module shifting cavity inside it. The needle module shifting cavity is provided with a needle module limiting end face at its left end. The needle module limiting end face is provided with a blood sampling puncture. The blood sampling puncture is provided with a contacting surface of blood sampling position at its outer edge. The inner sleeve is provided with a strip sliding wing in the top. The male fitting is provided on the strip sliding wing. The strip sliding wing is provided with a falcula fixing surface at its right end.

Preferably, the said needle module comprises a needle point protecting pole and a spring mounting pole. The spring is mounted on the spring mounting pole. The needle point protecting pole is provided with a reinforcement wing plate at its left end. The blood sampling puncture is provided with a reinforcement wing plate groove inside it. The needle point protecting pole is a hexagonal prism and is provided with an indentation that is apt to be broken.

The reinforcement wing plate provides a convenience to apply twisting force. The indentation enables the needle point protecting pole to be easily separated from actuating main body after twisting and allow the needle point to expose.

Preferably, the spring mounting pole is a cylinder and is provided with a needle point exposure length adjusting column at its right end.

According to the difference between the skin thickness and blood sampling quantity of each person, the puncturing depth and size are also different. The size of wound is decided by the outer diameter of needle tube, while the puncturing depth is related with the length of needle tube. In consideration of the uniform length L of puncturing needle tube for the convenience of production management, the right end of the spring mounting pole of needle module is designed as a cone form. The tail end of the cone form is provided with a needle point exposure length adjusting column. In production process, changing the length of said column on the plastic injection mould can correspondingly adjust the reference point where puncturing needle tube is placed in during plastic injection, thus changing the exposure depth of needle point after puncturing. When needle tube length L is a fixed value and the length of needle point exposed above the adjusting column is a, the needle exposure length is d; when the length of needle point exposed above the adjusting column is a1, the needle exposure length is d1; when the length of needle point exposed above the adjusting column is a2, the needle exposure length is d2; the smaller is the a value, the larger is the d value, indicating a larger puncturing depth.

Preferably, the said jacket is provided with an inner sleeve shifting cavity inside it at its left end. The inner sleeve shifting cavity is provided with a falcula-oriented slant at its top and bottom of right end. The jacket is provided with a spring mounting pole shifting hole inside it at its right end. The spring mounting pole shifting hole is provided with a spring limiting step inside it. The spring limiting step is provided with a spring mounting hole at its left side and with a spring mount pole extending hole at its right side. The aperture of spring mounting hole 141 is larger than that of spring mount pole extending hole. The diameter of spring is larger than the aperture of spring mount pole extending hole. Outside of the jacket is provided with a male fitting shifting groove. The male fitting shifting groove is provided with a male fitting limit reinforcement at its left side.

Preferably, the spring mounting pole is provided with an antiskid convex reinforcement. The wall of spring mounting hole is provided with a convex reinforcement.

Four antiskid convex reinforcements may be distributed along the circumference direction of spring mounting pole to fix the spring and prevent loosening. Four convex reinforcements may be used to prevent spiral spring to loosen inside the spring mounting hole.

Preferably, the strip sliding wing of inner sleeve is provided with a sliding wing slant at its right end. The actuating main body is provided with a slant at its right end.

The design of sliding wing slant can avoid generating disturbance to the shifting of falcula-oriented slant of the casing; actuating main body slant can avoid generating disturbance to falcula shifting to facilitate the falcula to shift along falcula-oriented slant and be separated from the inner sleeve.

Preferably, the exterior front and rear walls of inner sleeve are provided with an automatic assembling convex reinforcement. The front and rear walls of jacket is provided with a square indentation at its left end and with an antiskid convex reinforcement at its right end.

The convex reinforcements for automatic assembly are indispensable to the production equipment for automatic assembly, and the square indentation is the sliding groove of the convex reinforcements for automatic assembly. Several parallel antiskid convex reinforcements may be set up to prevent skidding in hand.

In the course of assembly, first allow the needle point protecting pole to pass the blood sampling hole of inner sleeve and the falcula hooking surface to cling to the falcula fixing surface. The spiral spring is nested on the spring mounting pole; male fittings are provided in the top and bottom of inner sleeve. The distance between two male fittings is slightly more than the distance between two male fitting limit reinforcements in the top and bottom of casing. Forcibly push the inner sleeve and enable the male fittings to be fitted with the male fitting shifting grooves, thus completing the assembly.

During operation, hold the casing with one hand and twist the reinforcement wing plate outside the inner sleeve with the other hand so that the needle point protecting pole and actuating main body are separated and the needle point is exposed. Press disinfected blood sampling position against the blood sampling hole and hold the casing with the other hand and press the hemostix against the blood sampling position, the spiral spring is compressed and the inner sleeve skids into the casing. The falcula skids to contact the falcula-oriented slant and then is forced to shift to the axial line along the falcula-oriented slant. The falcula hooking surface is separated from falcula fixing surface; After being separated from the restriction of inner sleeve, the needle module will rush to the blood sampling hole under the elasticity of compressed spiral spring; The needle point will penetrate the blood sampling hole and pierce the skin of blood sampling position. The limiting interface of actuating main body will restrict the shifting end of actuating main body, thus controlling the needle point puncturing depth. After the spiral spring releases compressed elasticity to enable the needle point to complete piercing and blood sampling, the spiral spring will restore natural length, generate withdrawing force and bring the needle point into the inner sleeve, thus fixing the inner sleeve and the casing and achieving the dual effects of eliminating the possibility of repeated use and safe protection.

According to the technical solution of the present invention, only by twisting reinforcement wing plate, aligning with blood sampling hole and pushing the case, can the operation of blood sampling be completed in a simple and easy way. After piercing, the needle point will withdraw into the inner sleeve, and both the inner sleeve and the casing will be fixed to completely prevent the repeated use of needle. In addition, the present invention can also control the depth of needle piercing.

DETAILED DESCRIPTION OF THE PREFERRED EMBODIMENTS

Reference will now be made in detail to exemplary embodiments of the invention with reference to the accompanying FIG. 1-13.

Example 1

Figure 1:
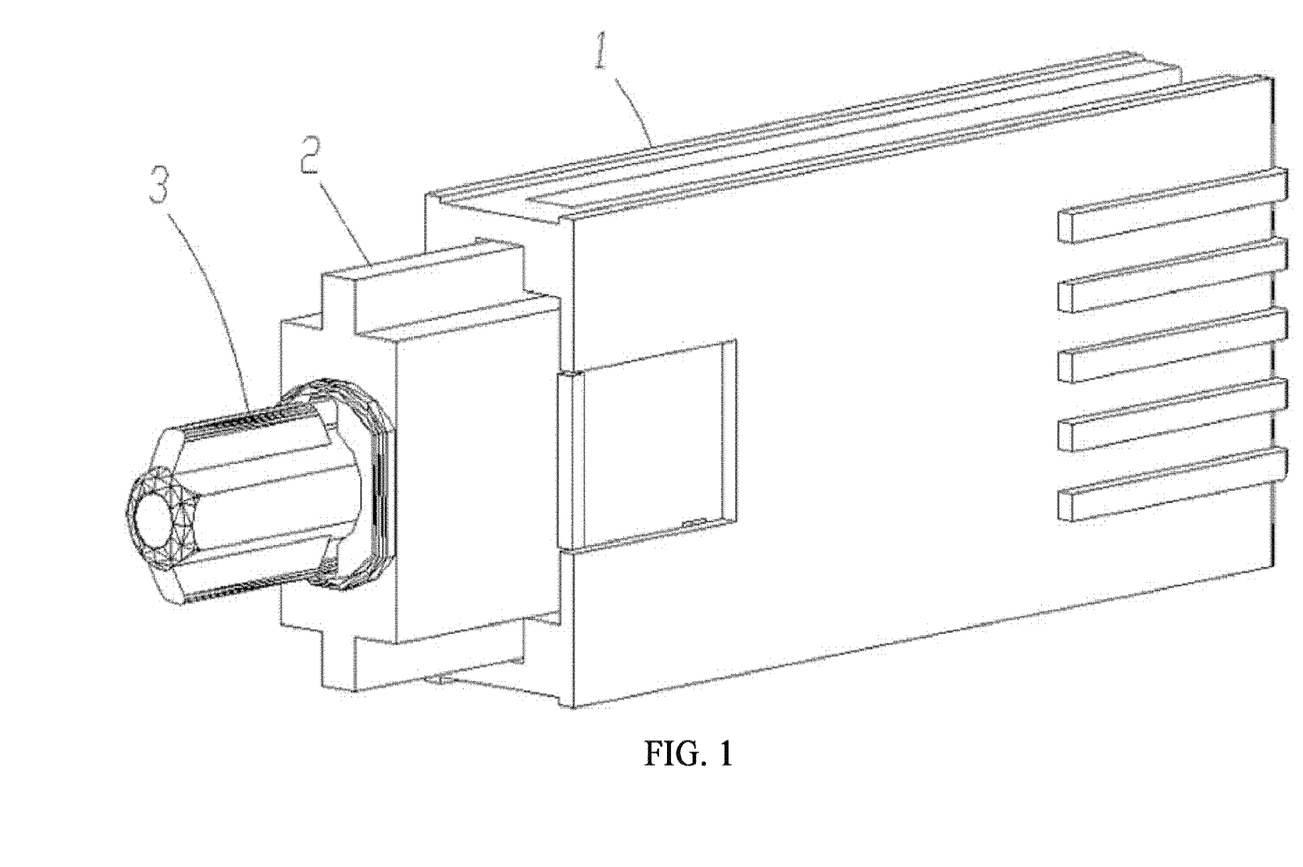
FIG. 1 is a schematic view of example 1 of the present invention.
Figure 2:
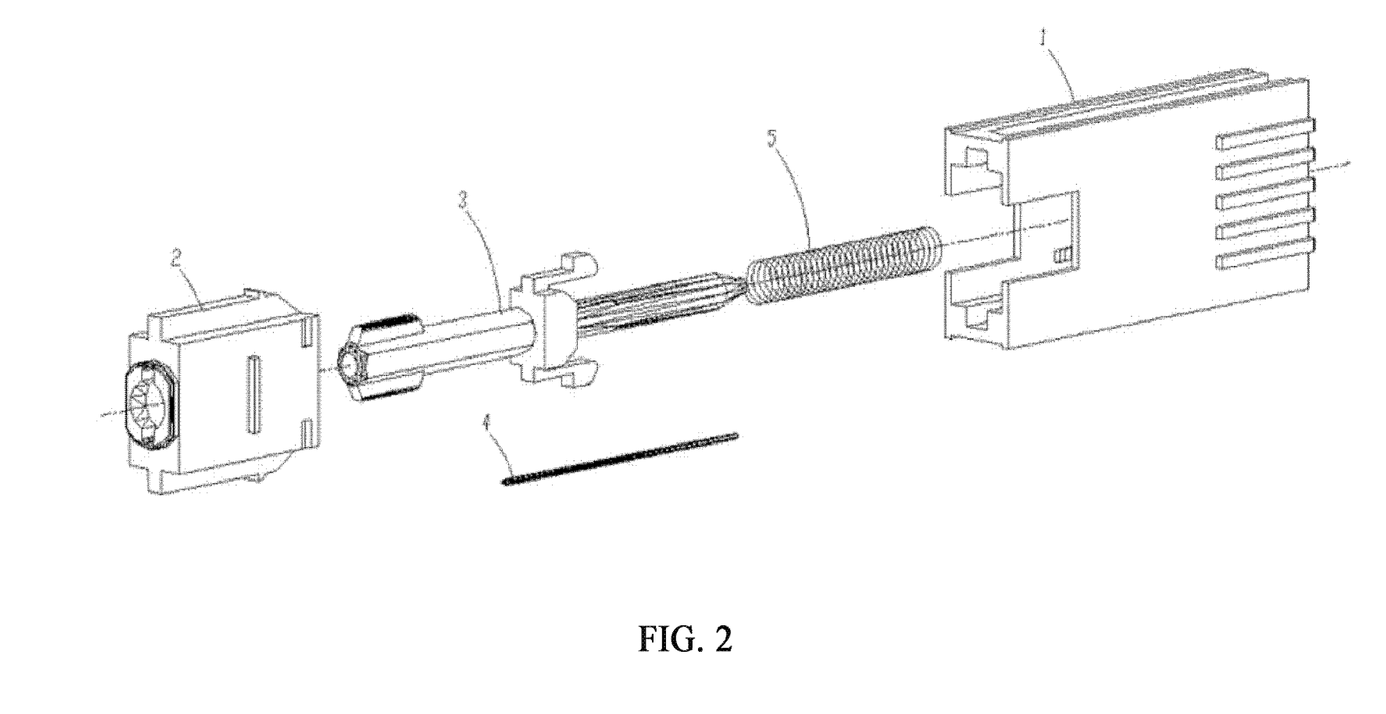
FIG. 2 is an exploded schematic view of FIG. 1.

A disposable automatic painless safe hemostix comprises a jacket 1, an inner sleeve 2, needle module 3 and a spring 5. A puncturing needle tube 4 is provided inside the needle module 3. One end of the said needle module 3 is nested in the inner sleeve 2 and other end extends in the jacket 1. The inner sleeve 2 is provided with a falcula fixing surface 23 and a male fitting 25. The needle module 3 is provided with a falcula 34. The inner wall of jacket 1 is provided with a falcula-oriented slant 133 and a male fitting limit reinforcement 12. One end of the falcula 34 fits the falcula fixing surface 23 and the other end fits the falcula-oriented slant 133.

Figure 5:
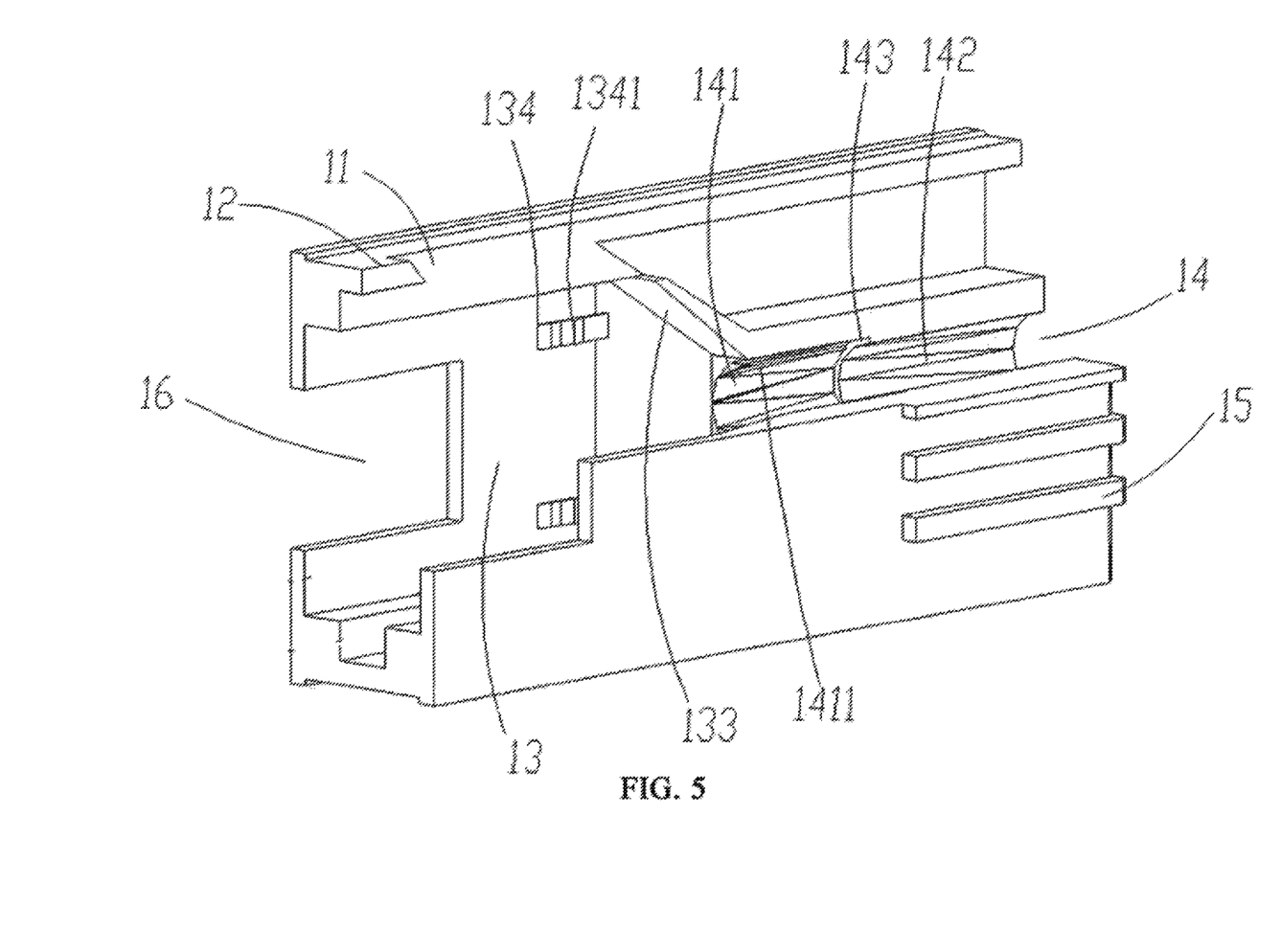
FIG. 5 is a schematic view of jacket of FIG. 1.
Figure 6:
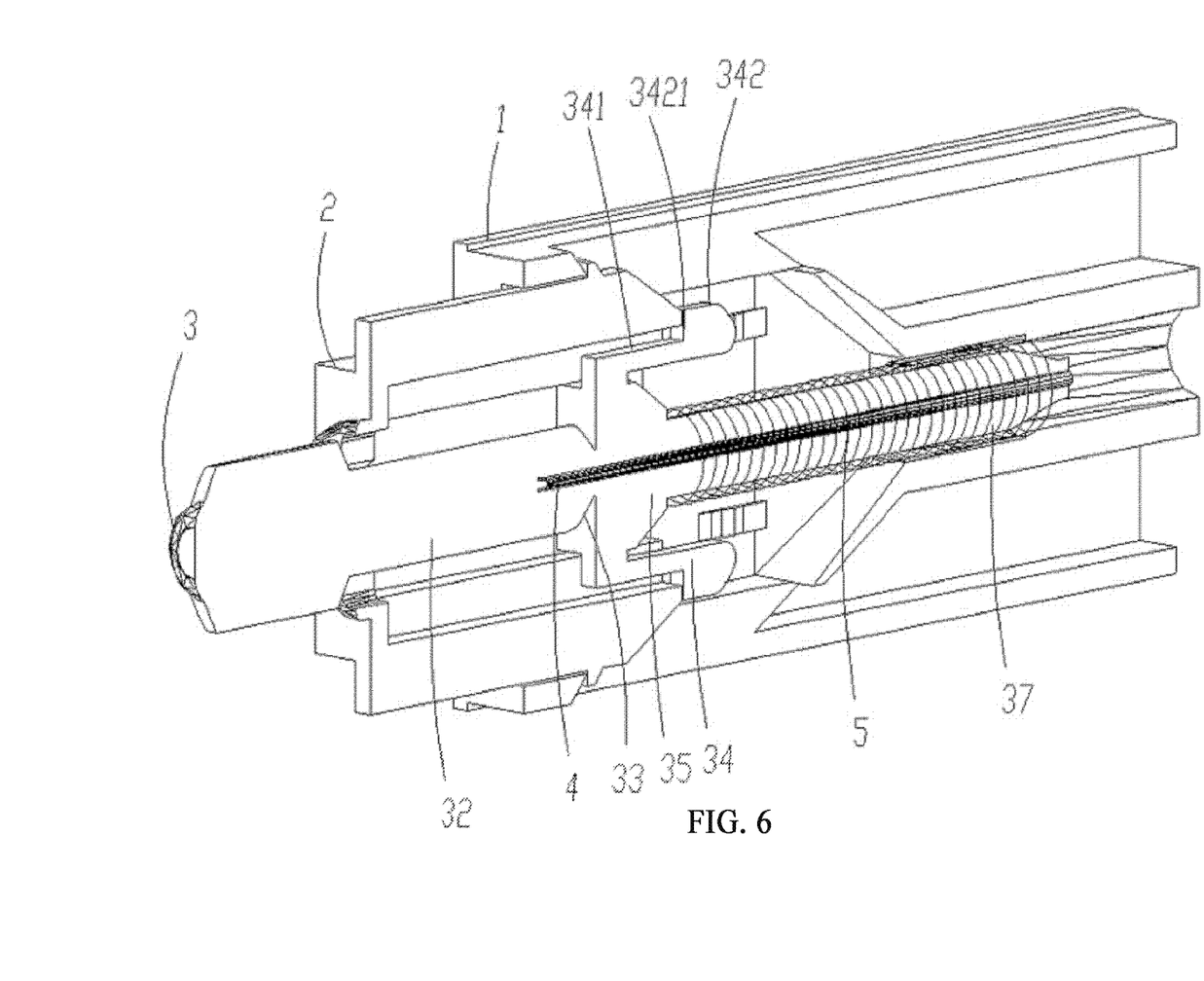
FIG. 6 is a schematic view of internal structure of FIG. 1.
Figure 7:
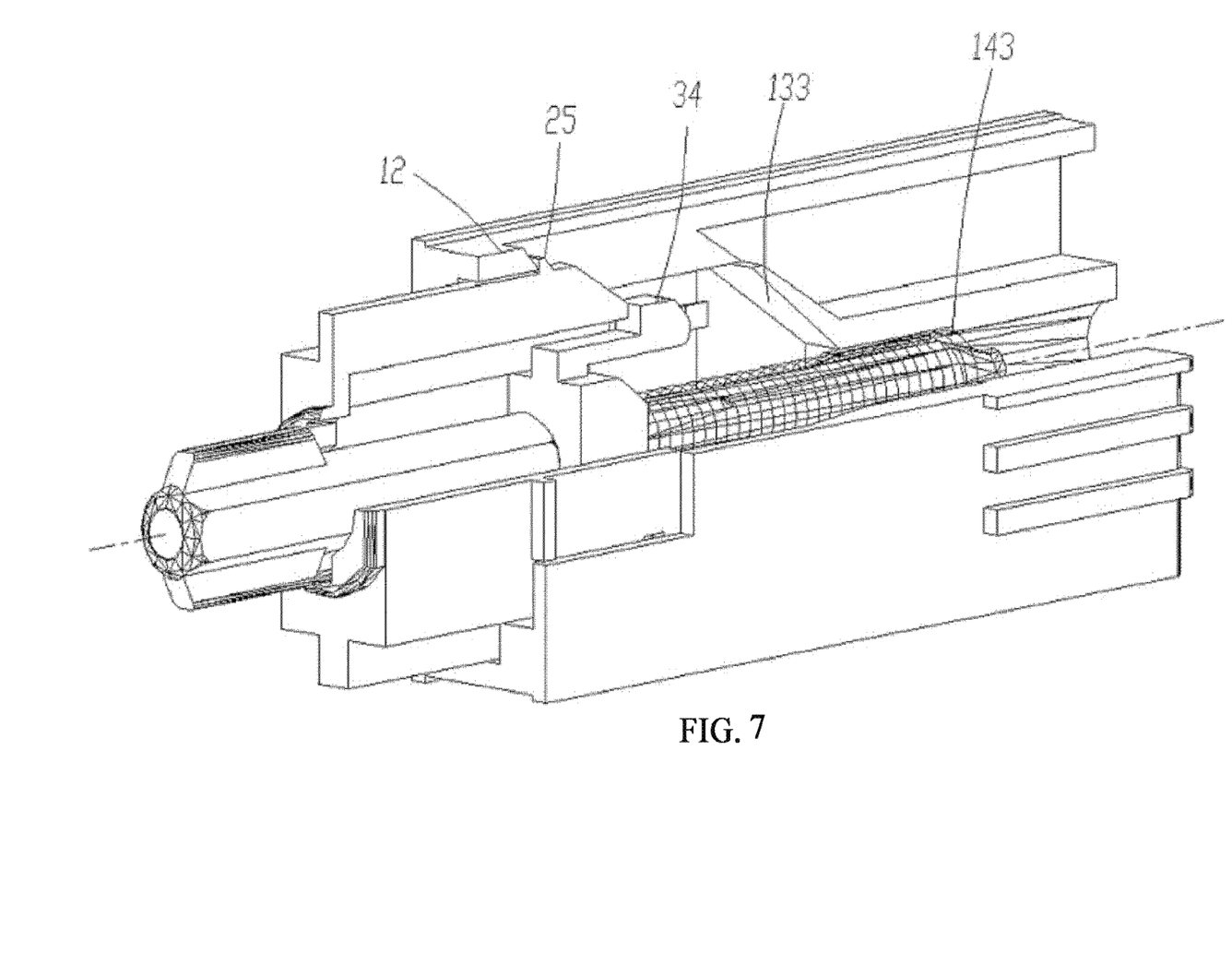
FIG. 7 is a schematic view of internal structure of FIG. 1.
Figure 8:
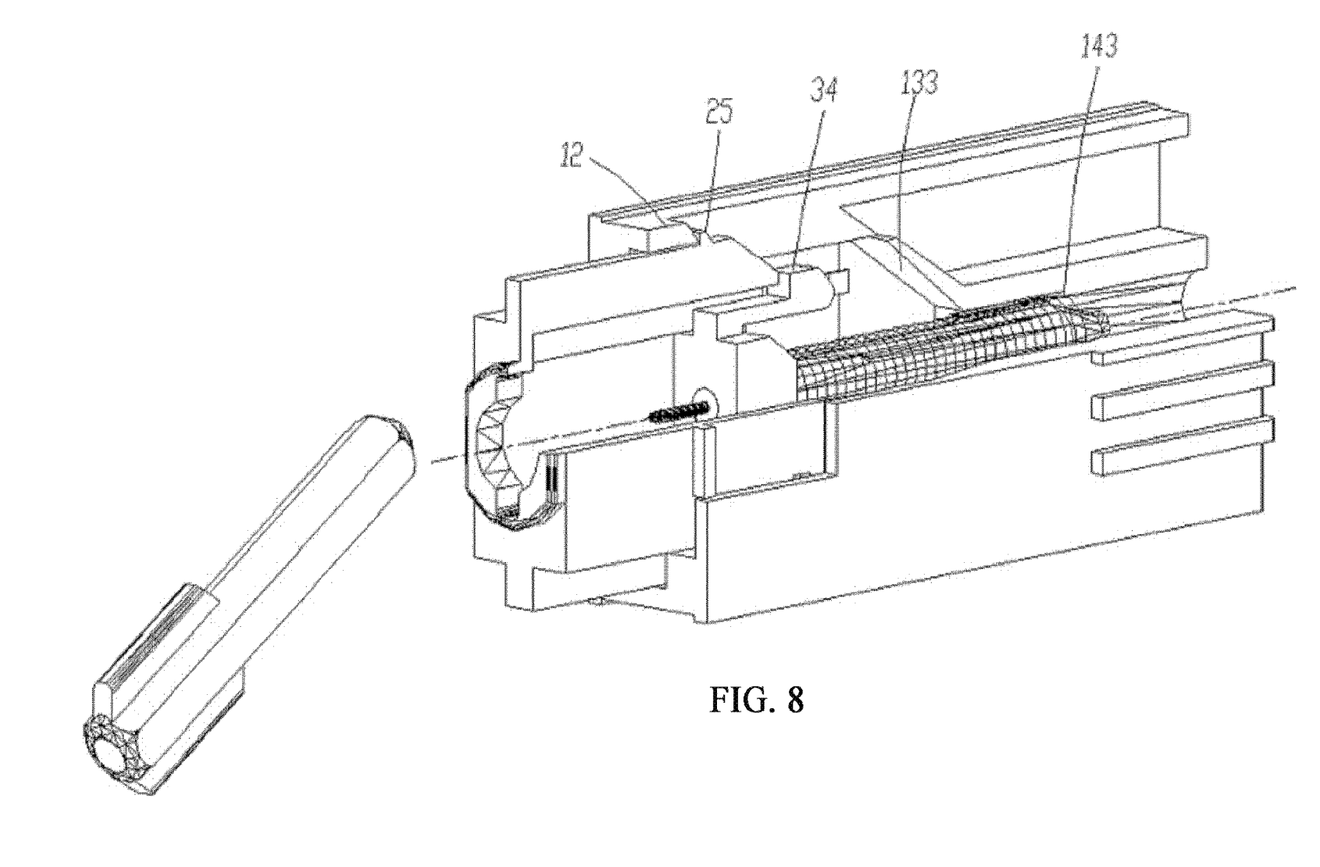
FIG. 8 is a schematic view of exposed needle point after the needle point protector is twisted off.
Figure 9:
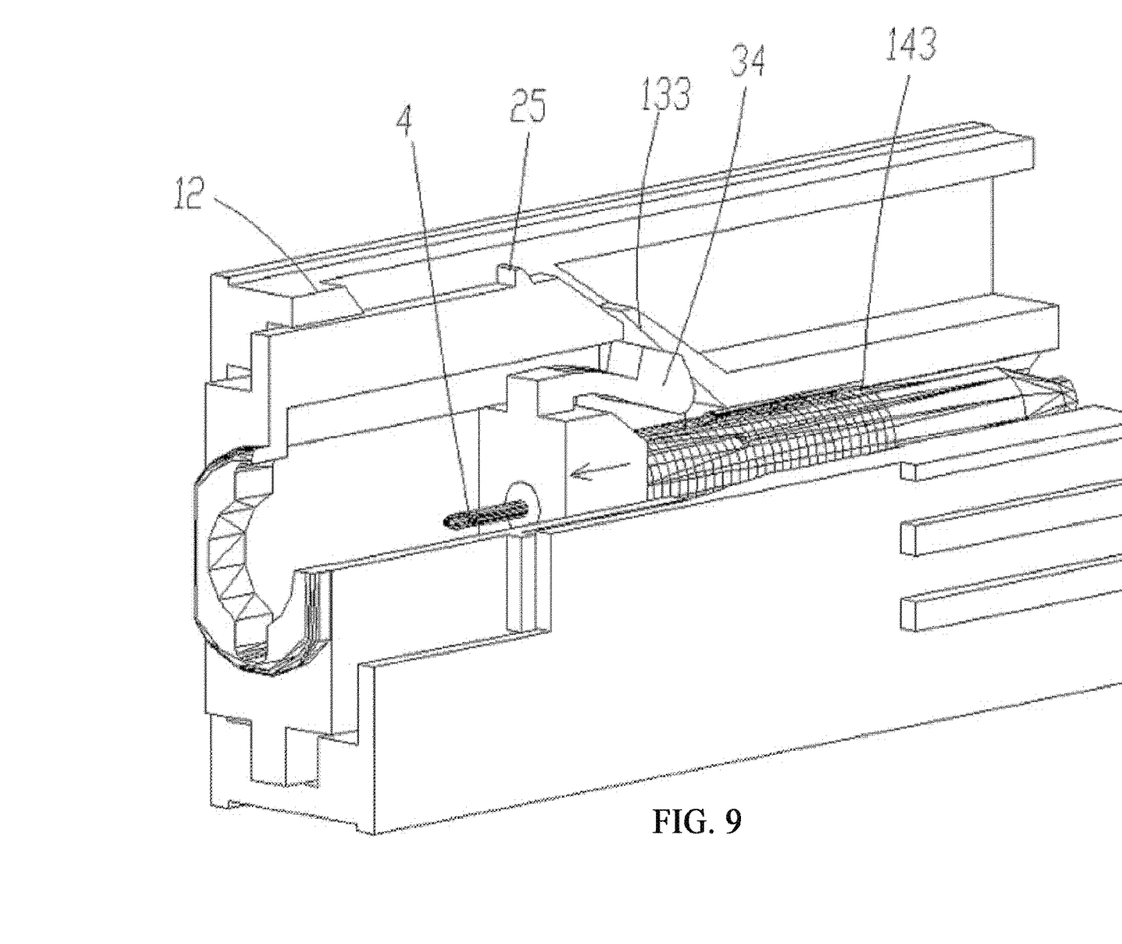
FIG. 9 is a schematic view of jacket shifting to the left while the falcula shifting along falcula-oriented slant and separating with the inner sleeve.
Figure 10:
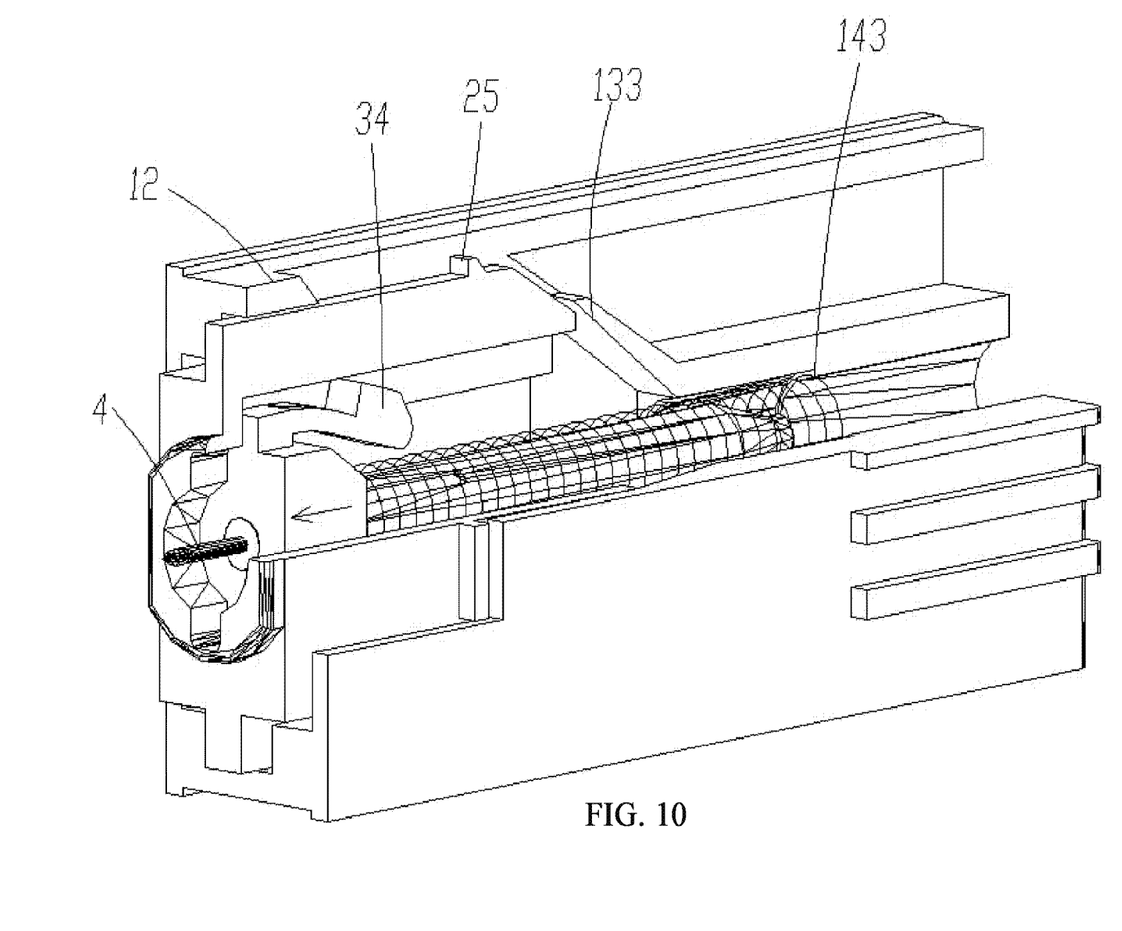
FIG. 10 is a schematic view of spring releasing elasticity and needle point passing through a blood sampling puncture.
Figure 11:
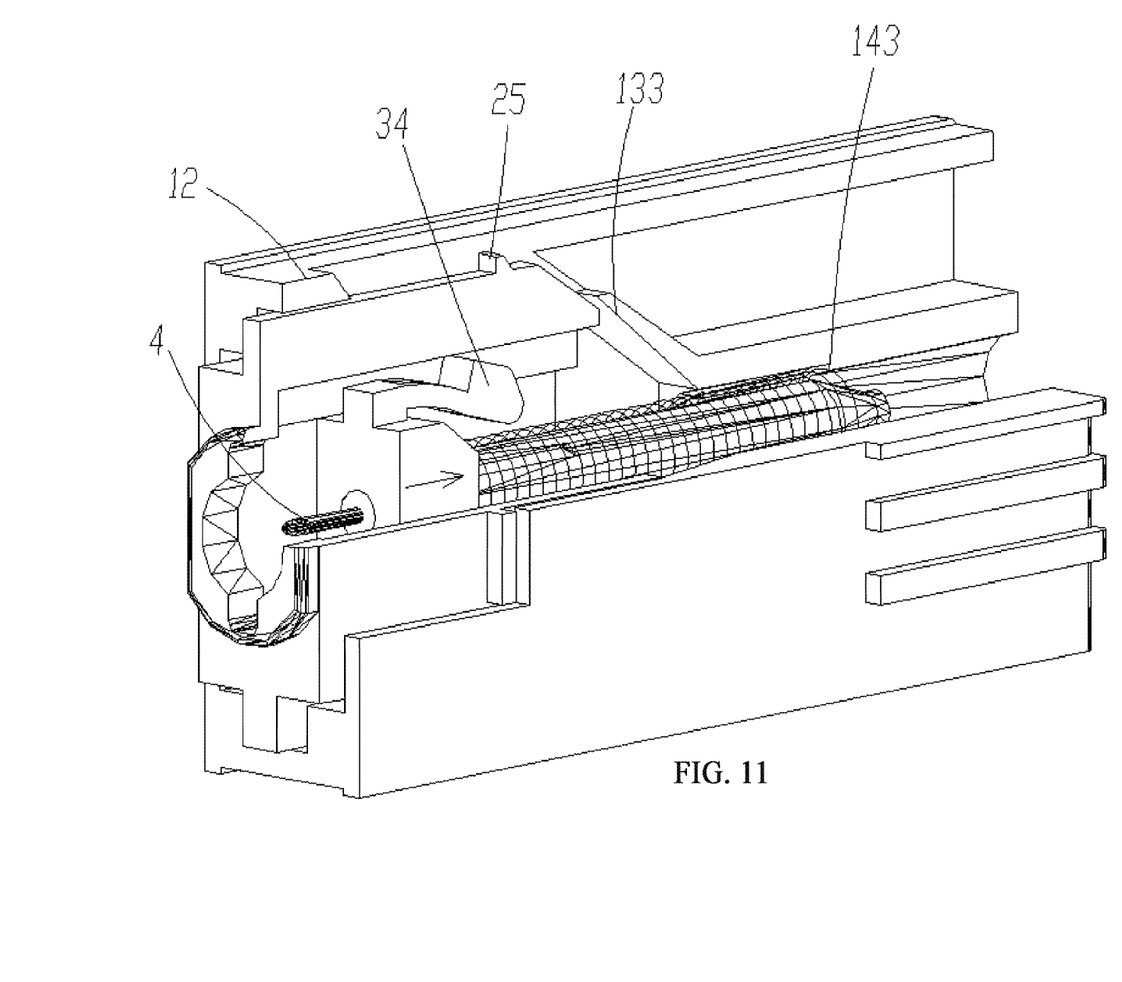
FIG. 11 is a schematic view of spring restoring natural length and needle point retracting in the inner sleeve.
Figure 12:
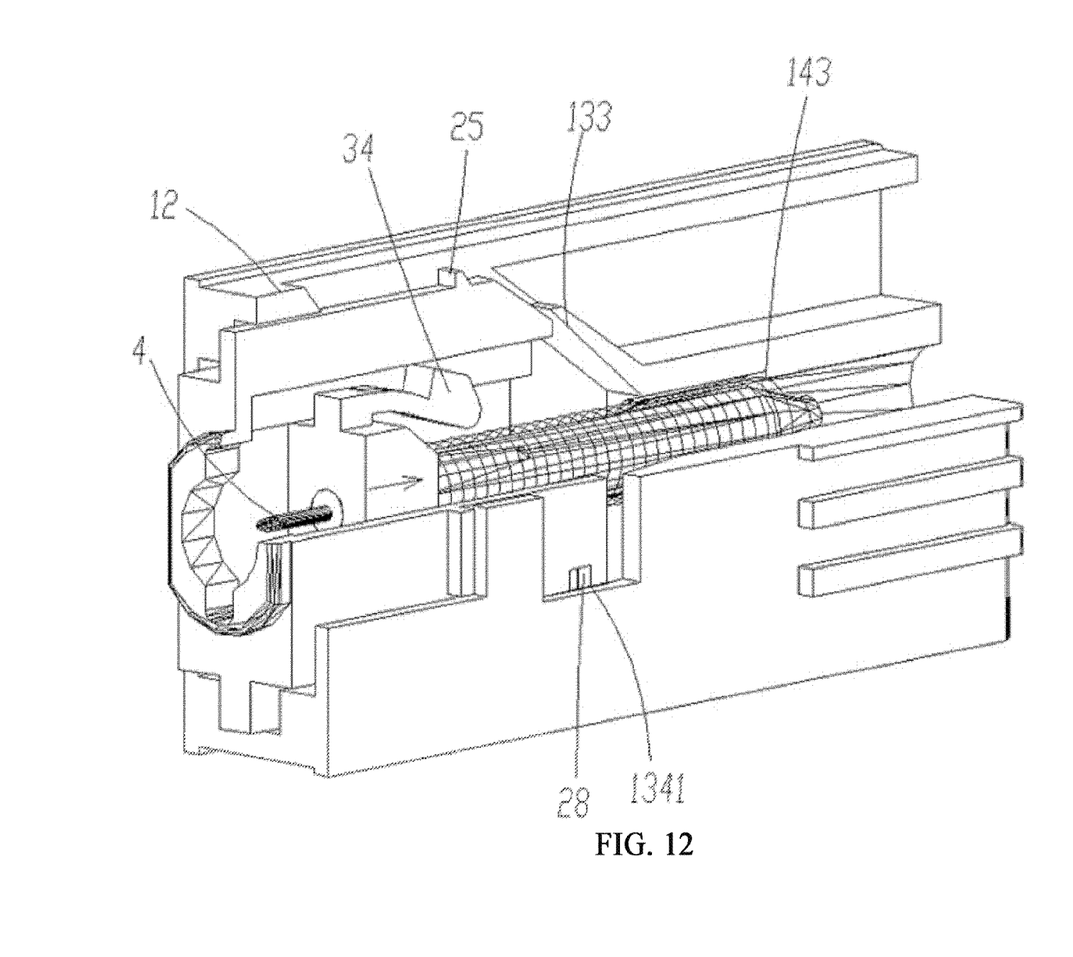
FIG. 12 is a schematic view of inner sleeve interlocking with jacket.

The inner wall of jacket 1 is provided with an inner sleeve closed fixing convex reinforcement 134. The inner sleeve closed fixing convex reinforcement 134 is provided with an emboss 1341. The outer wall of inner sleeve 2 is provided with a groove 28 that fits the emboss 1341.

Figure 3:
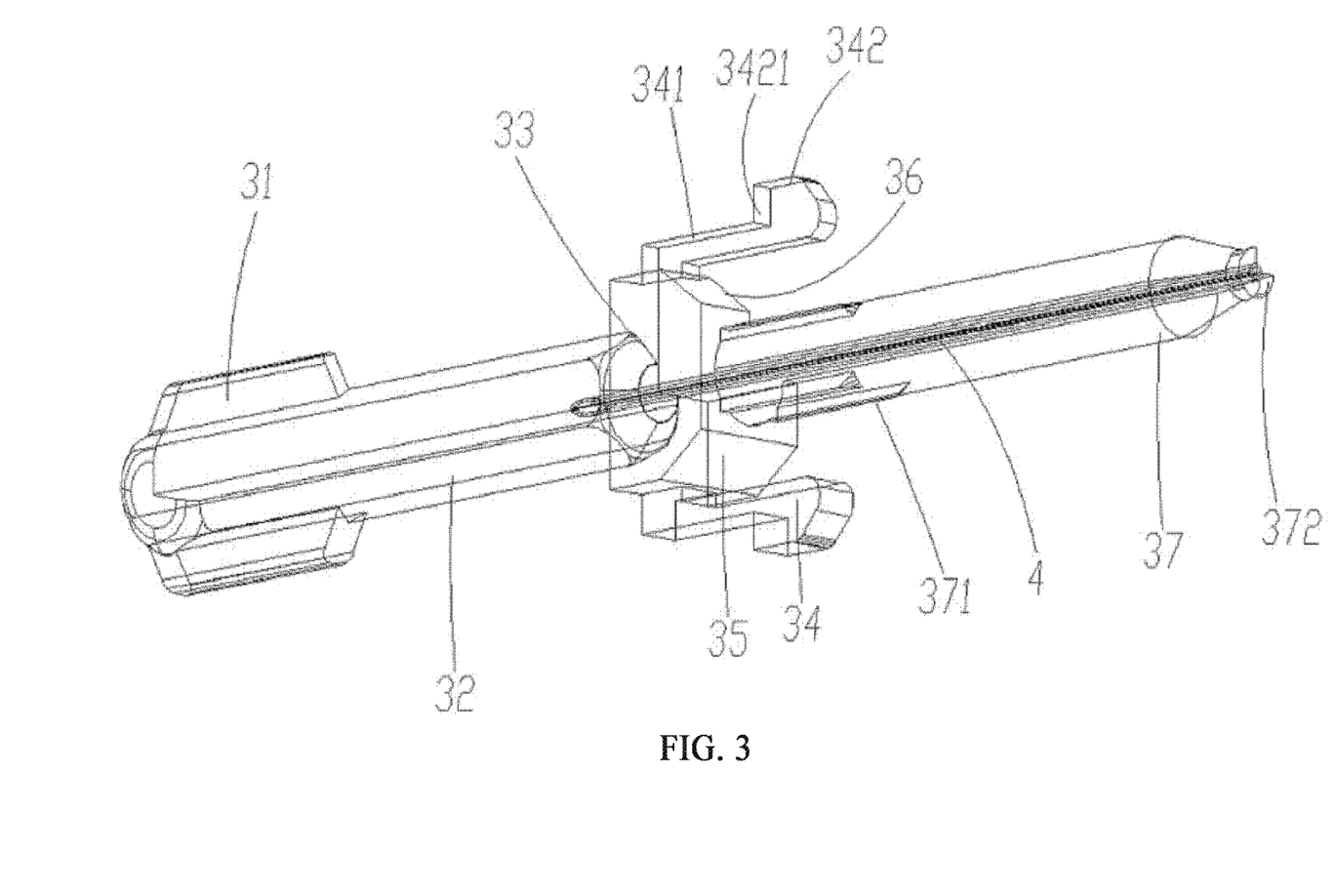
FIG. 3 is a schematic view of needle module of FIG. 1.

The said falcula 34 comprises a falcula connecting reinforcement 341 and a falcula button 342. The falcula connecting reinforcement 341 is connected with the falcula 34 and extends to the right end. The falcula button 342 is provided at the right end of falcula connecting reinforcement 341 and is also provided with a falcula hooking surface 3421 to fit the falcula fixing surface 23.

Figure 4:
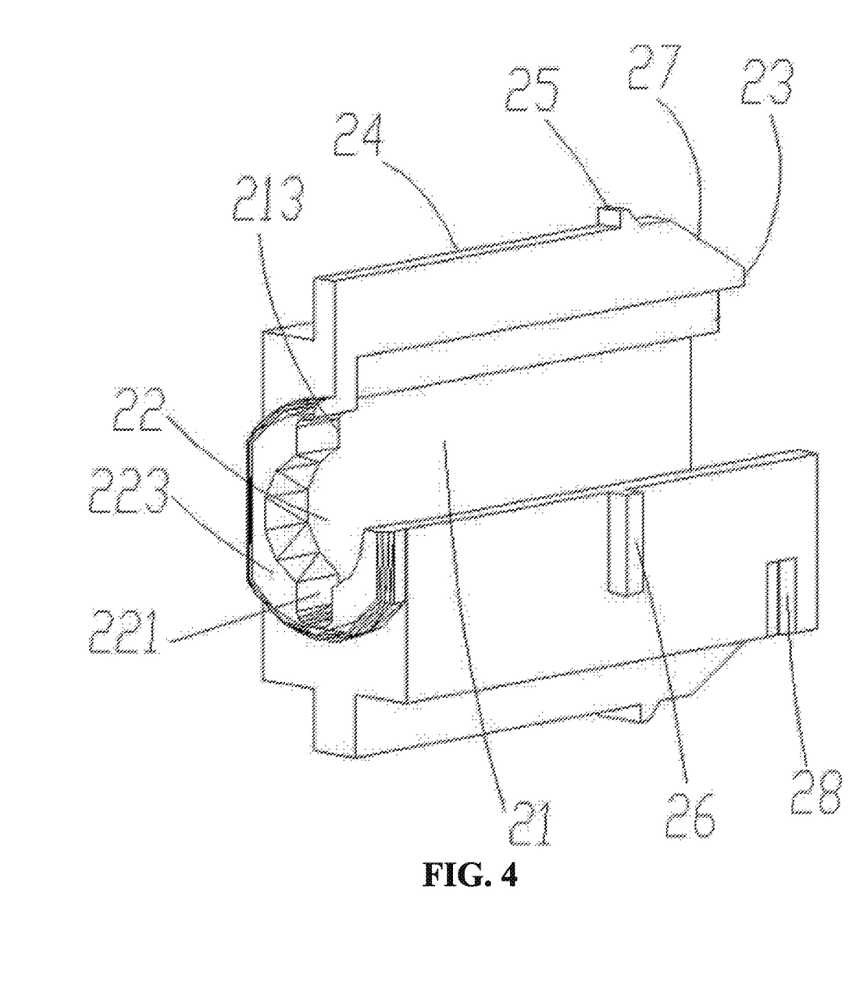
FIG. 4 is a schematic view of inner sleeve of FIG. 1.

The said inner sleeve 2 is provided with a needle module shifting cavity 21 inside it. The needle module shifting cavity 21 is provided with a needle module limiting end face 213 at its left end. The needle module limiting end face 213 is provided with a blood sampling puncture 22. The blood sampling puncture 22 is provided with a contacting surface 223 of blood sampling position at its outer edge. The inner sleeve 2 is provided with a strip sliding wing 24 in the top. The male fitting 25 is provided on the strip sliding wing 24. The strip sliding wing 24 is provided with a falcula fixing surface 23 at its right end.

The said needle module 3 comprises a needle point protecting pole 32 and a spring mounting pole 37. The spring 5 is mounted on the spring mounting pole 37. The needle point protecting pole 32 is provided with a reinforcement wing plate 31 at its left end. The blood sampling puncture 22 is provided with a reinforcement wing plate groove 221 inside it. The needle point protecting pole 32 is a hexagonal prism and is provided with an indentation 33 that is apt to be broken.

Figure 13:
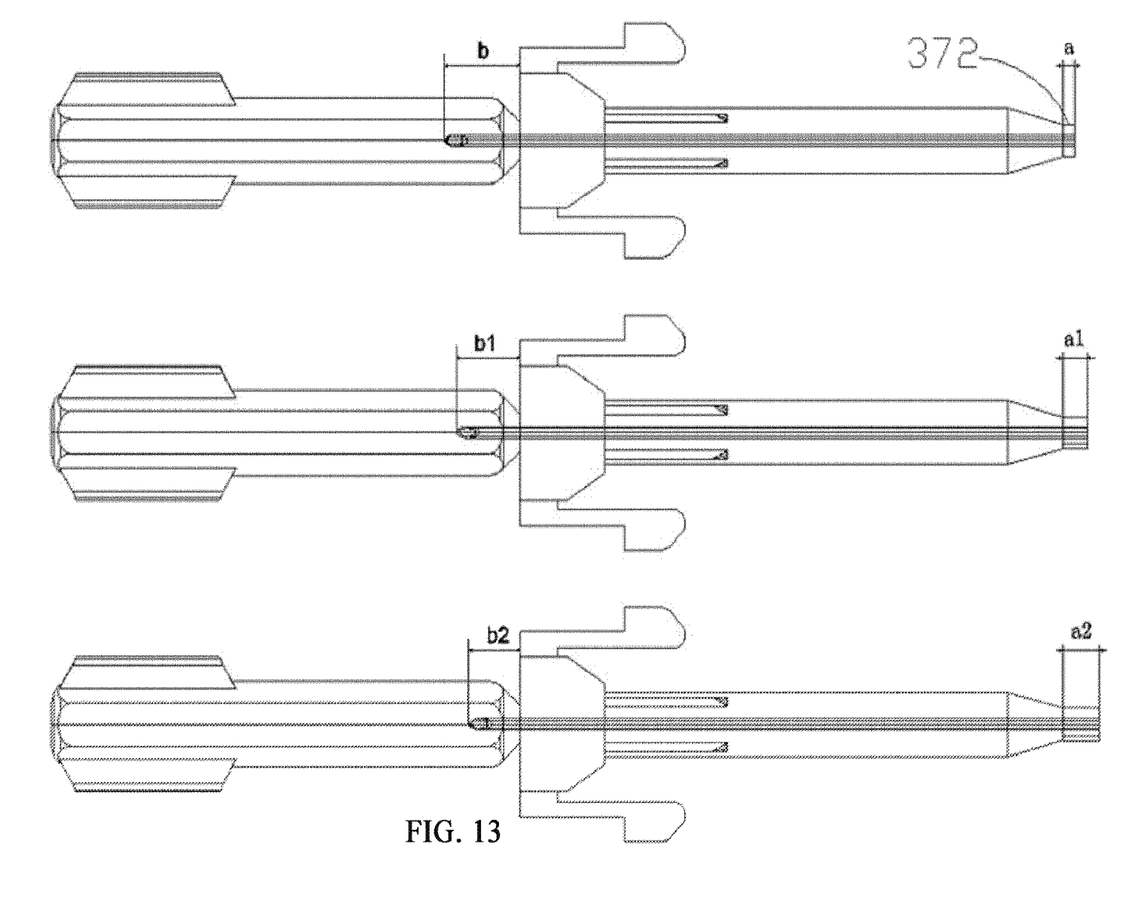
FIG. 13 is a schematic view of adjusting column adjusting the exposure length of needle point.

The spring mounting pole 37 is a cylinder and is provided with a needle point exposure length adjusting column 372 at its right end.

The said jacket 1 is provided with an inner sleeve shifting cavity 13 inside it at its left end. The inner sleeve shifting cavity 13 is provided with a falcula-oriented slant 133 at its right end. The jacket 1 is provided with a spring mounting pole shifting hole 14 inside it at its right end. The spring mounting pole shifting hole 14 is provided with a spring limiting step 143 inside it. The spring limiting step 143 is provided with a spring mounting hole 141 at its left side and with a spring mount pole extending hole 142 at its right side. The aperture of spring mounting hole 141 is larger than that of spring mount pole extending hole 142. The diameter of spring 5 is larger than the aperture of spring mount pole extending hole 142. The jacket 1 is provided with a male fitting shifting groove 11. The male fitting shifting groove 11 is provided with a male fitting limit reinforcement 12.

The spring mounting pole 37 is provided with an antiskid convex reinforcement 371. The wall of spring mounting hole 141 is provided with a convex reinforcement 1411. The outer diameter of spring 5 is larger than the diagonal inner diameter of convex reinforcement 1411 on the inner wall of spring mounting hole 141, while the inner diameter of spring 5 is smaller than the diagonal inner diameter of antiskid reinforcement 371 on the spring mounting pole 37.

The strip sliding wing 24 of inner sleeve 2 is provided with a sliding wing slant 27 at its right end. The actuating main body 35 is provided with a slant 36 at its right end.

The exterior front and rear walls of inner sleeve 2 are provided with a convex reinforcement 26 for automatic assembly. The front and rear walls of jacket 1 is provided with a square indentation 16 at its left end and with an antiskid convex reinforcement 15 at its right end.

In summary, the above-mentioned examples are only preferred examples of the present invention. All the changes and modifications are to be understood as being included within the scope of the present invention as defined by the appended claims.

What is claimed is:

1. A disposable automatic painless safe hemostix, comprising:
   a jacket (1) having:
      an inner sleeve shifting cavity (13),
      top, bottom, left side, and right side inner walls,
      two falcula-oriented slants (133) provided on one of the inner walls of the jacket (1),
      two male fitting shifting grooves (11) with a male fitting limit reinforcement (12) provided on the top and bottom inner walls of the jacket (1) respectively,
      two square indentations (16) provided on the left side and right side inner walls respectively,
      two inner sleeve closed fixing convex reinforcements (134) provided on the left side inner wall and another two inner sleeve closed fixing convex reinforcements (134) provided on the right side inner wall of the jacket, each inner sleeve closed fixing convex reinforcement (134) comprising an emboss (1341);
   an inner sleeve (2) having:
      a body being moveable in the inner sleeve shifting cavity (13),
      two convex reinforcements (26) respectively provided on left and right side walls of the inner sleeve (2) being moveable in the square indentations (16);
      two grooves (28) provided on the left side wall of the inner sleeve and another two grooves (28) provided on the right side wall of the inner sleeve (2), each groove (28) receiving one of the embosses (1341),
      two strip sliding wings (24) respectively provided on top and bottom was of the inner sleeve (2) being moveable in the two male fitting shifting grooves (11) respectively,
      two falcula fixing surfaces (23) and two male fittings (25) provided on the two strip sliding wings (24) respectively;
   a needle module (3) nested into the inner sleeve (2) having:
      a puncturing needle tube (4),
      two falculas (34), each falcula (34) comprises a falcula connecting reinforcement (341), a falcula button (342) and a falcula hooking surface (3421), each falcula hooking surface (3421) contacts one of the falcula fixing surfaces (23) and each falcula button (342) fits one of the falcula-oriented slants (133),
      a needle point protecting pole (32) provided with an indentation (33) and two reinforcement wing plates (31);
   a spring (5) provided on the needle module (3);
   a sleeve-jacket locking means comprising the grooves (28) of the inner sleeve (2) and the embosses (1341) of the jacket (1), wherein the inner sleeve (2) and the jacket (1) are locked together when the embosses (1341) enter into the grooves (28).

2. The disposable automatic painless safe hemostix according to claim 1, wherein the inner sleeve (2) has a needle module shifting cavity (21) provided with a needle module limiting end face (213), the needle module limiting end face (213) is provided with a blood sampling puncture (22) having a contacting surface (223).

3. The disposable automatic painless safe hemostix according to claim 1, wherein the needle module (3) comprises a spring mounting pole (37), and the spring (5) is mounted on the spring mounting pole (37), wherein a blood sampling puncture (22) is provided with a reinforcement wing plate groove (221), the needle point protecting pole (32) is a hexagonal prism.

4. The disposable automatic painless safe hemostix according to claim 3, wherein the spring mounting pole (37) is a cylinder.

5. The disposable automatic painless safe hemostix according to claim 1, wherein a spring mounting pole shifting hole (14) is in the inner sleeve shifting cavity (13), the spring mounting pole shifting hole (14) is provided with a spring limiting step (143), a spring mounting hole (141) and a spring mount pole extending hole (142).

6. The disposable automatic painless safe hemostix according to claim 5, wherein a spring mounting pole (37) of the needle module (3) is provided with an antiskid convex reinforcement (371) and a wall of the spring mounting hole (141) is provided with a convex reinforcement (1411).

* * * * *